(12) United States Patent
Bertram et al.

(10) Patent No.: US 8,483,363 B2
(45) Date of Patent: Jul. 9, 2013

(54) MOVABLE WEDGE FOR IMPROVED IMAGE QUALITY IN 3D X-RAY IMAGING

(75) Inventors: Matthias Bertram, Aachen (DE); Jens Wiegert, Aachen (DE); John F. Vesel, Kirtland, OH (US); David Sowards-Emmerd, Sunnyvale, CA (US); Michael J. Petrilo, Pleasanton, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 414 days.

(21) Appl. No.: 12/740,366

(22) PCT Filed: Nov. 4, 2008

(86) PCT No.: PCT/IB2008/054589
§ 371 (c)(1),
(2), (4) Date: Apr. 29, 2010

(87) PCT Pub. No.: WO2009/063353
PCT Pub. Date: May 22, 2009

(65) Prior Publication Data
US 2010/0308229 A1    Dec. 9, 2010

Related U.S. Application Data

(60) Provisional application No. 60/988,153, filed on Nov. 15, 2007.

(51) Int. Cl.
*G21K 3/00* (2006.01)
(52) U.S. Cl.
USPC .......................................... 378/157; 378/145

(58) Field of Classification Search
USPC ........................................ 378/4–20, 145–159
See application file for complete search history.

(56) References Cited

U.S. PATENT DOCUMENTS

| | | | |
|---|---|---|---|
| 4,181,858 A | 1/1980 | Moore | |
| 6,501,828 B1 | 12/2002 | Popescu | |
| 6,542,576 B2 | 4/2003 | Mattson | |
| 6,618,466 B1 | 9/2003 | Ning | |
| 7,263,156 B2 * | 8/2007 | Roberts et al. | 378/14 |
| 2003/0147502 A1 * | 8/2003 | Heismann et al. | 378/156 |
| 2004/0030246 A1 * | 2/2004 | Townsend et al. | 600/427 |
| 2005/0013411 A1 | 1/2005 | Yahata et al. | |

(Continued)

FOREIGN PATENT DOCUMENTS

| | | |
|---|---|---|
| EP | 0146992 A1 | 7/1985 |
| GB | 2005514 A | 4/1979 |

OTHER PUBLICATIONS

Graham, S. A., et al.; Compensators for dose and scatter management in cone-beam computed tomography; 2007; Med. Phys.; 34(7)2691-2703.

*Primary Examiner* — Hoon Song (57) ABSTRACT

When generating a 3D image of a subject or patient, a cone beam X-ray source (*20a, 20b*) is mounted to a rotatable gantry (14) opposite an offset flat panel X-ray detector (*22a, 22b*). A wedge-shaped attenuation filter (*24a, 24b*) of suitable material (e.g., aluminum or the like) is adjustably positioned in the cone beam to selectively attenuate the beam as a function of the shape, size, and density of a volume of interest (18) through which X-rays pass in order to maintain X-ray intensity or gain at a relatively constant level within a range of acceptable levels.

22 Claims, 5 Drawing Sheets

U.S. PATENT DOCUMENTS

| | | | |
|---|---|---|---|
| 2005/0089137 A1* | 4/2005 | Toth et al. | 378/19 |
| 2005/0089139 A1 | 4/2005 | Sukovic | |
| 2005/0089146 A1 | 4/2005 | Toth et al. | |
| 2006/0291612 A1* | 12/2006 | Nishide et al. | 378/4 |
| 2007/0110210 A1 | 5/2007 | Nishide et al. | |
| 2008/0130823 A1* | 6/2008 | Hagiwara | 378/4 |

* cited by examiner

MOVABLE WEDGE FOR IMPROVED IMAGE QUALITY IN 3D X-RAY IMAGING

CROSS REFERENCE TO RELATED APPLICATIONS

This application claims the benefit of U.S. provisional application Ser. No. 60/988,153 filed Nov. 15, 2007, which is incorporated herein by reference.

The present application finds particular application in medical imaging and treatment systems, particularly involving cone-beam computed tomography (CT) and/or image-guided radiation therapy. However, it will be appreciated that the described technique may also find application in other imaging systems, other medical scenarios, or other medical techniques.

Many CT systems employ a compensator (bow-tie filter) to reduce X-ray scatter and patient dose during single or multi-slice CT scans. However, the compensators do not always fit to the size and shape of the imaged object and are not adjustable. In conventional CT, the bowtie-shaped element is positioned between the x-ray source and the examined subject. In radiation therapy imaging, a wedge-shaped element is similarly positioned. In cone-beam CT, in which the detector is offset to enlarge the field-of-view, no compensating element is used. In diagnostic CT, use of a compensator is standard due to its benefits on image quality. Similar benefits were described in a recent publication for cone-beam CT (S. A. Graham et al., Med. Phys. 34, 2691, 2007).

Fitting the compensator to the size and shape of the imaged object has proven difficult to achieve in practice. The compensator is commonly a machined aluminum block. The thickness of the block can be selected such that the line integral of attenuation through the block and a water phantom (e.g., a circular or elliptical cylinder) is constant. When the size or shape of the patient differs from that of the phantom, the compensation is less than ideal.

The present application provides new and improved compensator systems and methods that improve image quality, which have the advantages of adjustable X-ray filtering, and which overcome the above-referenced problems and others.

In accordance with one aspect, an imaging system includes a rotating gantry with an examination region in which a volume of interest (VOI) is positioned, and a transmission X-ray source, mounted for rotation with the gantry, the X-ray beam emitted across the examination region to an X-ray detector. The system further includes a movable wedge-shaped attenuation filter, positioned between the X-ray source and the examination region, for the wedge being movable relative to the X-ray beam to adjust an attenuation of the X-ray beams.

In accordance with another aspect, a method of generating a 3D image of a subject includes evaluating a VOI in an examination region of an X-ray imaging device to determine size, shape, and density information about a portion of the VOI in the examination region, and positioning an adjustable wedge-shaped attenuation filter at a position in a cone-shaped X-ray beam, the wedge-shaped attenuation filter being movable in front of the X-ray source. Once the wedge-shaped attenuation filter has been positioned, CT data acquisition and gantry rotation are initiated.

In accordance with yet another aspect, an apparatus for generating a 3D patient image includes means for generating a cone-shaped X-ray beam which traverses half of a VOI, such that the beam traverses the other half of the VOI when rotated 180°, and means for detecting the X-ray beam. The apparatus further includes means for adjustably attenuating of the X-ray beam, and means for monitoring size, shape, and density of the VOI presented to the X-ray beam during a 360° revolution of the X-ray generating means and means around the VOI. The apparatus further includes means for selectively adjusting X-ray attenuation by the attenuation means as the X-ray generation means and the detecting means rotate around the VOI.

One advantage is that the compensation or filtering is adjustable.

Another advantage resides in X-ray dose optimization.

Another advantage is that the filtering can be dynamically adjusted during a scan.

Another advantage resides in increased field of view relative to detector size.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

Figure 1:
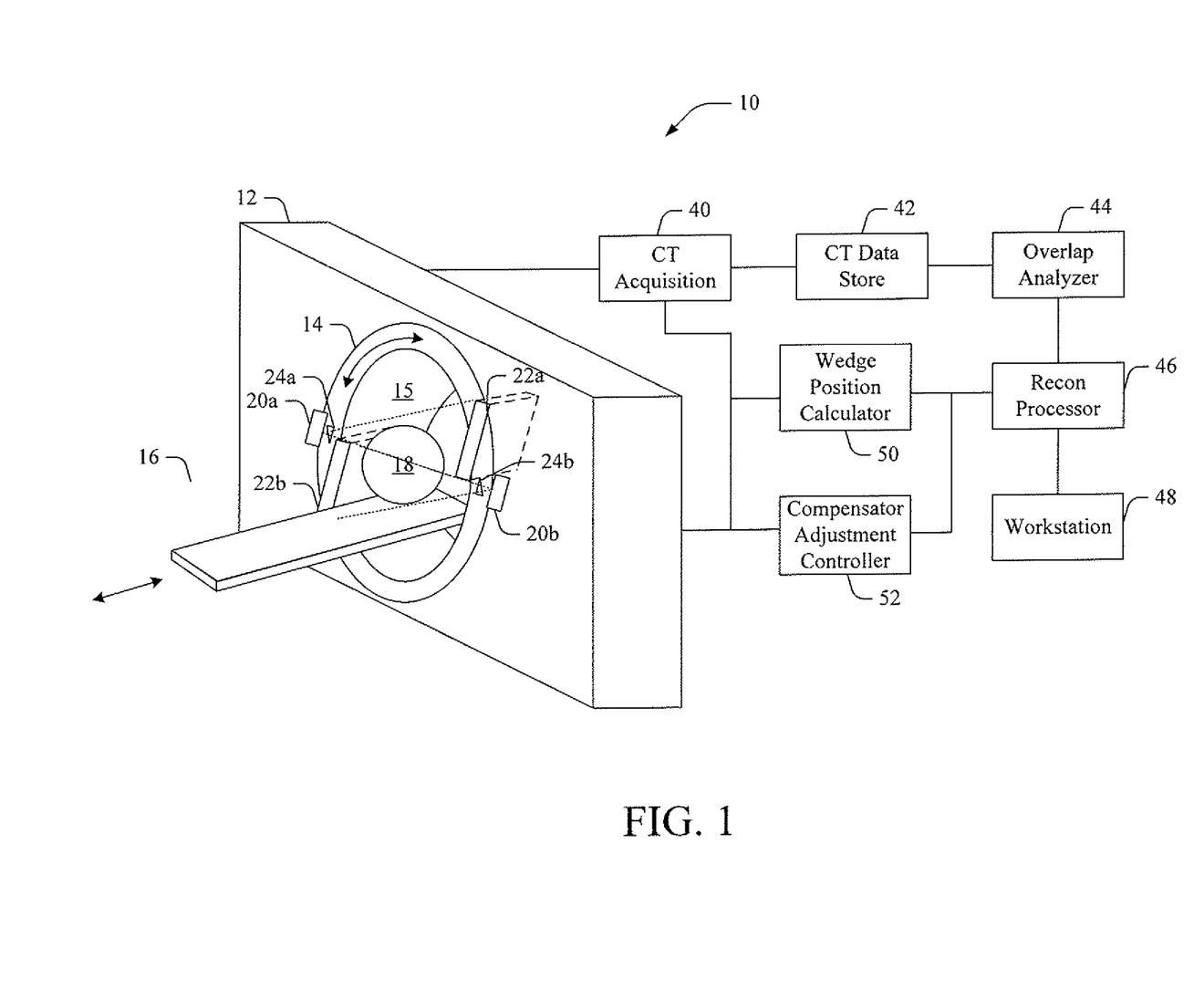
FIG. 1 illustrates an imaging system includes an imaging device, such as a computed tomography (CT) imager or the like, which includes a rotatable gantry with a bore there through, into which a subject support is inserted for imaging a volume of interest (VOI).

With reference to FIG. 1, an imaging system 10 includes an imaging device 12, such as a computed tomography (CT) imager or the like, which includes a rotatable gantry 14 defining a bore 15 extending therethrough, into which a subject support 16 is inserted for imaging a volume of interest (VOI) 18 of the subject. An X-ray source 20a is mounted to the gantry 14. The X-ray source emits a cone-beam of X-rays across an examination region in which the VOI is positioned. The cone-beam is received by an X-ray detector 22a, such as a flat panel X-ray detector. The detector is offset or misaligned relative to projected center of radiation. Specifically, the cone beam and the detector are offset such that half of the examination region is examined when the x-ray source and detector are in a first position 20a, 22a, and the other half is examined when the X-ray source and detector are in a second position 20b, 22b. Alternatively, two X-ray sources 20a, 20b, and two detectors 22a, 22b, can be provided. Systems with three or more source-detector pairs are also contemplated.

A wedge-shaped, or half-bowtie-shaped, attenuation filter 24a, 24b, is used in conjunction with the cone-beam X-ray source(s) 20a, 20b and offset detector(s) 22a, 22b. Moreover, the position of the wedge is adjustable in accordance with patient geometry. By shifting the position of the wedge, the thickness of the wedge through which each ray of x-rays passes is adjusted. The position of the wedge can be selected in various ways. For example, after a scout image is generated, a wedge position is selected which holds the line integral of the x-ray rays through the patient substantially constant. Alternatively, the position can be estimated from the protocol, such as a head position versus torso position. Further, the wedge can be moved dynamically during a scan to adjust for different projections through an elliptical body portion or VOI. The gantry rotates 360° to generate multiple views of the VOI to ensure that a complete X-ray data set is available for reconstruction into a viewable image. The wedge(s) 24a, 24b, can be formed of Aluminum (Al), Molybdenum (Mo), Teflon, or some other suitable material.

The system 10 further includes a CT acquisition module 40 that receives detected X-ray data from the imaging device 12, and a CT data store 42 that stores and/or buffers raw X-ray data. An overlap analyzer 44 resolves redundant data if the cone beams overlap slightly to ensure that a complete data set is present for the VOI. For example, redundant rays can be weighted and combined. A reconstruction processor 46 reconstructs an image of the VOI, for instance using a filtered back-projection reconstruction technique for viewing by an operator on a workstation 48.

In one embodiment, the contour of the subject perimeter and a density map are determined from a pilot scan. A wedge position calculator 50 monitors the VOI to determine the shape, size, position, and density of the VOI. A compensator adjustment controller 52 receives information from the wedge position calculator and adjusts the wedge(s) 24a, 24b accordingly to compensate for the size, shape, and density of the imaged portion of the subject. For example, the X-ray detector has a range of X-ray intensities over which it is designed to operate, and the wedge(s) can be adjusted to manipulate attenuation or gain so that X-rays are received at the detector at an intensity level that is within the detector's range. The controller 52 can adjust the wedge(s) so that a line integral of X-ray attenuation through the wedge and irradiated portion of the subject is relatively constant and results in a radiation intensity at a selected point or in a selected region in the detector's operating range (e.g., a mid-point). In a dynamically adjusted embodiment, as the gantry rotates during CT acquisition, the path length and density through the VOI will change as seen from the X-ray source(s). These path length and density changes are determined by the wedge position calculator 50, and the controller 52 adjusts the wedge (s) accordingly. Wedge positions can be calibrated at a fixed number of wedge positions, and intermediate wedge positions can be interpolated there from. For example, the reconstruction processor can send pilot scan information to the calculator and the controller, which operate to reposition the wedge according to the path length and density changes.

In one embodiment, the system 10 is employed in conjunction with a C-arm X-ray system (not shown) (e.g., X-ray source, image intensifier, and video read-out system) with offset detector, and/or for radiation therapy devices with an on-board imager. For use on a C-arm system, the wedge may be shifted outside the beam if not needed for certain parts of an examination. In another embodiment, patient-specific optimized beam shaping is achieved by positioning the movable wedge (or half bow-tie), and adjusting the lateral position of the wedge according to the patient's attenuation profile. "Lateral," as used herein, describes movement across the X-ray cone beam, as indicated by the arrow in FIG. 2. The wedge position may either be fixed during the entire scan (e.g., an optimized position may either be pre-specified by the scan protocol or be determined using image processing algorithms according to the attenuation distribution in a pilot scan before the imaging scan), or the wedge may be moved relative to the source during the scan. Alternatively, in hybrid cone-beam CT (CBCT) systems with positron emission tomography (PET) or single photon emission computed tomography (SPECT), an optimal wedge position may be derived from the PET or SPECT image. For instance, nuclear detector heads (not shown), such as PET or SPECT detector heads, can be movably coupled to the gantry 14. PET or SPECT data captured by the detector heads can be reconstructed into corresponding image data, which is then used to identify an optimal wedge position for CT data acquisition.

In SPECT imaging, a projection image representation is defined by the radiation data received at each coordinate on the detector head. In SPECT imaging, a collimator defines the rays along which radiation is received. In PET imaging, the detector head outputs are monitored for coincident radiation events on two heads. From the position and orientation of the heads and the location on the faces at which the coincident radiation is received, a ray between the coincident event detection points is calculated. This ray defines a line along which the radiation event occurred. In both PET and SPECT, the radiation data from a multiplicity of angular orientations of the heads is stored to data memory, and then reconstructed by a reconstruction processor into a transverse volumetric image representation of the region of interest, which is stored in a volume image memory.

For proper gain correction, air scans, water scans, and bone equivalent scans may be acquired for different reproducible positions of the wedge to calibrate a plurality of wedge positions, and image gain corrections for intermediate positions of the wedge may be interpolated.

The lateral position of the wedge is a parameter for its beam shaping function and can be adjusted before or during a CBCT scan according to the detected attenuation distribution of the patient (e.g., the larger the patient or patient portion, the thinner the wedge portion that is positioned in the X-ray beam). In this manner, a "one wedge fits all patients" scenario can be realized.

In another embodiment, a single cone-beam X-ray source is positioned on the gantry opposite an offset flat panel X-ray detector, with a wedge positioned between the X-ray source and an examination region in which the VOI is positioned. The beam emitted by the X-ray source can pass through approximately half or more of the VOI, and a complete X-ray data set can be collected as the gantry rotates through a 360° revolution. The wedge can be adjusted as the gantry rotates to maintain relatively constant attenuation line integrals for X-ray paths through the VOI to keep the image gain substantially constant, which turn facilitates reconstruction of an image with good contrast.

Figure 2:
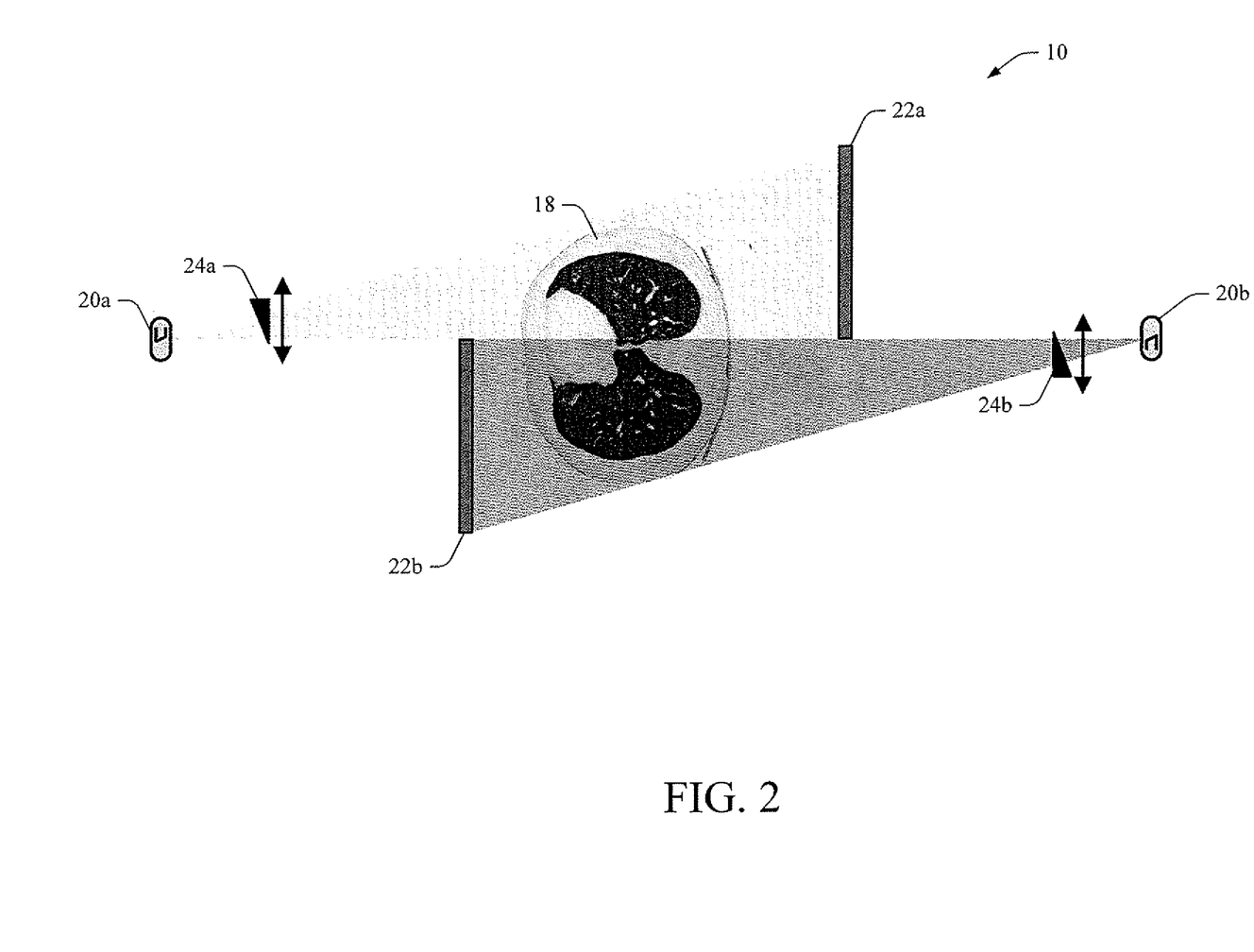
FIG. 2 is a diagrammatic illustration of a rotational dual X-ray source and offset detector portion of the system (or a single source and detector system illustrated concurrently in 180° opposite positions.

FIG. 2 is an illustration of the X-ray source and offset detector portion of the system 10, illustrated concurrently at 180° opposite positions (a) and (b). The two X-ray source positions 20a, 20b generate cone-shaped X-ray beams in opposite orientations to generate a field of view (FOV) that encompasses the VOI 18 (e.g., a human thorax in this example). Each X-ray cone is received at a flat-panel detector 22a, 22b, and is generated using a filter and/or collimator (not shown) to create a desired cone shape. To change the lateral position of the wedge 24a, 24b with respect to the source and the detector in a reproducible way, various mechanical means may be employed. In one embodiment, the means for its automated translation of the wedges is integrated into the collimator of the particular X-ray system employed.

Additionally, different means may be employed to determine an optimal lateral position of the wedge for a given shape and size of the VOI. In one embodiment, the position of the wedge is fixed during the CBCT acquisition, and is determined before the scan either depending on the chosen scan protocol (e.g., different pre-determined positions for scans of the head, the torso, the periphery, and/or pediatric protocols, etc.), or depending on information extracted from a scout projection or low-dose scan. In the latter case, the relevant parameters, in particular the spatial dimensions (width and depth) of the object and the position of its projected boundary, are extracted from the attenuation profile using image processing techniques, and the wedge is optimally placed according to these parameters.

In other embodiments, the position of the wedge is automatically adjusted during the scan, depending on the information extracted in real-time from the acquired projections. Additionally or alternatively, in a hybrid CBCT system with SPECT or PET, the optimal location of the wedge may be derived from the PET or SPECT image. For proper gain correction and correction of the beam hardening and scattering effects of the wedge, calibrations may be made beforehand for different positions of the wedge. In a scenario where continuous shifting of the wedge is desired, appropriate calibration images may be obtained by means of interpolation between the calibration images acquired at a number of fixed positions.

Figure 3:
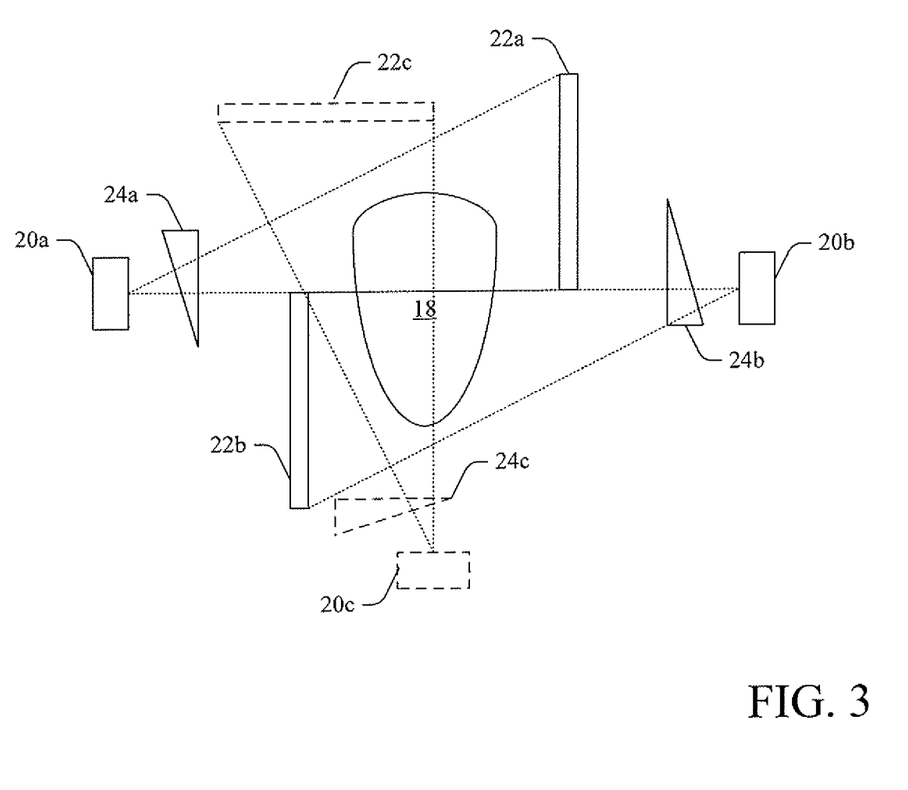
FIG. 3 illustrates another configuration of the dual CBCT scanning system, in which one wedge has been shifted to increase the width or thickness of the wedge material through which the beam emitted by the X-ray source travels in accordance with an asymmetrically thinner portion of the VOI.

FIG. 3 illustrates another configuration of the CBCT scanning system 10, illustrated concurrently at 180° opposite positions (a) and (b), in which the wedge is shifted to adjust the width/thickness of the wedge material through which the beam travels in accordance with a path length through the VOI at different rotational positions. For instance, an intermediate-thickness portion of the VOI is positioned in the field of view of the X-ray source position 20a, and the wedge 24a is positioned with a central portion in the beam to attenuate the cone beam in accordance with the relative thickness of the VOI. A thinner portion of the VOI is positioned in the field of view of the X-ray source at 20b, and the wedge 24b is positioned with a thicker portion in the X-ray beam, to increase attenuation of the beam emitted by the second X-ray source so that line integrals for the X-rays through the thinner portion of the VOI are substantially equal to line integrals for X-rays through the thicker portion of the VOI. Analogously, when the X-ray source at 20c projects the X-ray beam through the longest paths through the VOI, the wedge 24c is shifted such that its thinnest portion is in the beam. In this manner, a complete set of accurate X-ray data can be collected with relatively constant intensity over a single gantry revolution, and the VOI is subjected to less radiation than would otherwise be present (e.g., in a multi-revolution CT scan).

Figure 4:
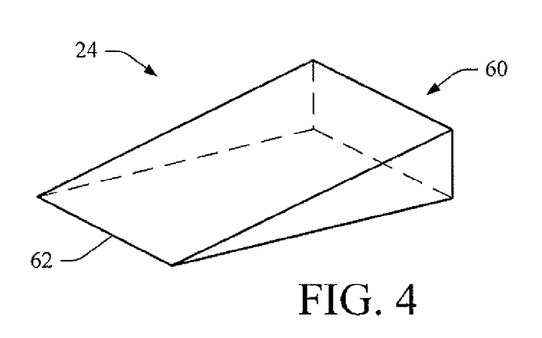
FIG. 4 illustrates one embodiment of the wedge, in which the wedge has a typical wedge shape, including a substantially rectangular base and four sides that taper to an edge opposite the base.

FIG. 4 illustrates one embodiment of the wedge 24, in which the wedge has a typical wedge shape, including a substantially rectangular base 60 and top and bottom sides that taper to an edge 62 opposite the base. As the wedge position is adjusted in front of an X-ray source, the thickness of the wedge material changes, thereby altering beam hardness or energy content of the X-ray cone beam. It will be appreciated that the wedge 24 is not limited to having the illustrated geometry, and that any suitable geometry may be used in conjunction with the systems and/or methods described herein.

Figure 5:
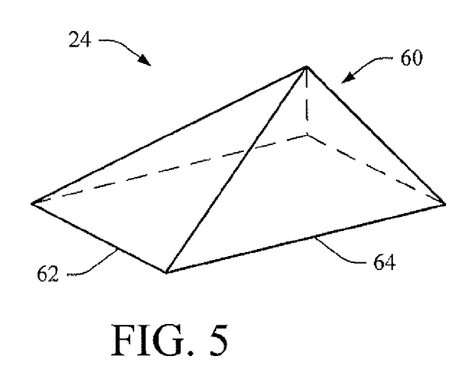
FIG. 5 illustrates another embodiment of the wedge in which the base is triangular, and the four sides taper to two edges.

FIG. 5 illustrates another embodiment of the wedge 24 in which the base 60 is triangular, and two top surfaces taper to edges, 62 and 64. This configuration permits cone-beam adjustment in two planes as the position of the wedge 24 is adjusted in front of an X-ray source.

Figure 6:
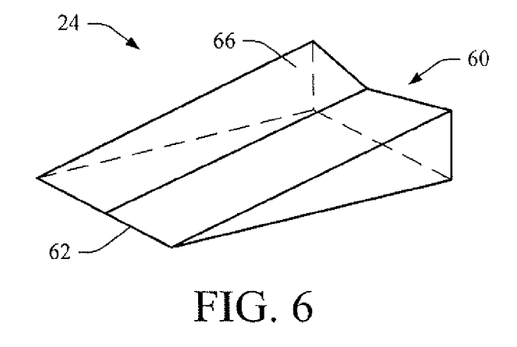
FIG. 6 illustrates another embodiment of the wedge in which the base has a bow-tie-like shape and the sides of the wedge taper to the edge.

FIG. 6 illustrates another embodiment of the wedge 24 in which the base 60 has a bow-tie-like shape and the sides of the wedge taper to the edge 62. In this embodiment, the top surface 66 has a crease running approximately down the center of the surface between the base and the edge 62. This causes the wedge to be thinner in the center than at the sides along a longitudinally axis from the base 60 to the edge 62, which permits further manipulation of the X-ray beam as wedge position is manipulated.

Figure 7:
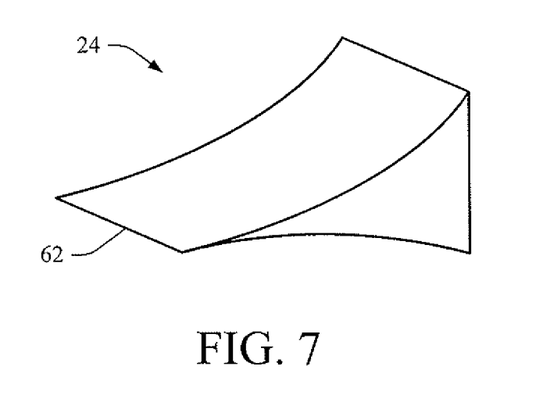
FIG. 7 illustrates another wedge embodiment.

FIG. 7 illustrates an embodiment of the wedge 24 in which the top and bottom surfaces are non-planar.

Figure 8:
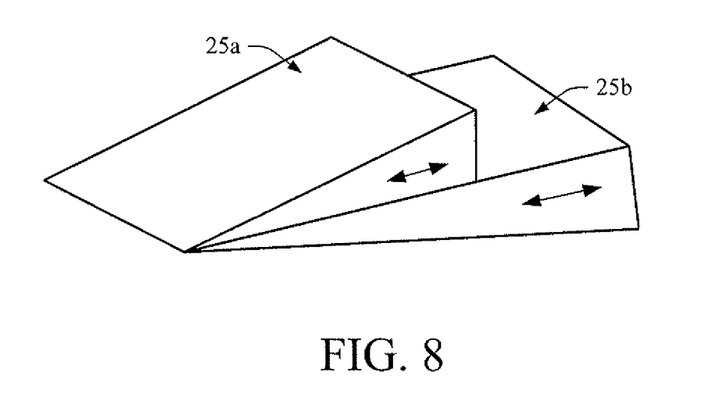
FIG. 8 illustrates a dual wedge embodiment.

FIG. 8 illustrates an embodiment in which two wedges 25a, 25b are positioned with flat bottom or other surfaces contiguous to each other. The two wedges can be moved independently for greater freedom in the adjustment of the attenuation properties. In another embodiment, a mechanically adjustable wedge has an adjustable slope that can be manipulated to adjust attenuation of the X-ray beam.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. An imaging system, including:
    a rotating gantry with an examination region in which a volume of interest (VOI) is positioned;
    a transmission X-ray source, mounted for rotation with the gantry, the X-ray beam emitted across the examination region to an X-ray detector; and
    a movable wedge-shaped attenuation filter comprising a first lateral portion having a first thickness exposed to the X-ray beam, a second lateral portion having a second thickness exposed to the X-ray beam wherein the first thickness is greater than the second thickness, and a middle portion extending from the first lateral portion to the second lateral portion and having a thickness exposed to the X-ray beam which continually decreases from the first thickness to the second thickness,
    wherein the filter is positioned between the X-ray source and the examination region, for the filter being at least laterally movable relative to the X-ray beam to adjust an attenuation of the X-ray beam across an entire lateral extent of the X-ray beam between the first lateral portion and the second lateral portion of the filter.

2. The system according to claim 1, wherein the X-ray source generates a half field of view across the VOI and generates a complementary half field of view when the gantry is rotated 180°.

3. The system according to claim 1, wherein the wedge-shaped attenuation filter is movable, closer to or further from the X-ray source.

4. The system according to claim 1, wherein the X-ray detector is a flat panel X-ray detector, and wherein the gantry rotates 360° to generate a complete set of X-ray data for the VOI during computed tomography (CT) acquisition.

5. The system according to claim 4, further comprising an overlap analyzer that compensates for redundant data collected along redundant rays during the 360° rotation of the gantry to refine the X-ray data.

6. The system according to claim 5, further comprising a reconstruction processor that reconstructs a CT image of the VOI from the refined X-ray data.

7. The system according to claim 1, further including a wedge position calculator that determines path length and density information encountered by the X-ray beam at each rotational position of the X-ray source.

8. The system according to claim 7, further comprising a controller that receives path length and density information in real time and adjusts the position of the wedge-shaped attenuation filter during rotation.

9. The system according to claim 8, wherein the wedge position calculator calculates wedge position as a function of X-ray gain detected at the detector, and path length and density information.

10. The system according to claim 1, wherein the wedge-shaped attenuation filter has a rectangular base, two opposite triangular sides that connect to the base and taper to an edge opposite the base, and two rectangular sides that connect to the base and the edge opposite the base.

11. The system according to claim 1, further including at least two nuclear detector heads movably mounted to the gantry, wherein the nuclear detector heads are at least one of positron emission tomography (PET) detector heads or single-photon emission computed tomography (SPECT) detector heads.

12. The system according to claim 1, wherein the X-ray source is a cone-beam X-ray source.

13. The system according to claim 1, wherein the wedge-shaped attenuation filter has at least one of the following configurations:
- a base with a pseudo-bow-tie shape, coupled to a top surface with a substantially central crease running the length thereof to an edge that is common to a bottom surface;
- a rectangular base that is coupled to curved top and bottom surfaces that meet at a common edge; or
- a dual-wedge arrangement, wherein a first wedge and a second wedge are slidably and adjustably coupled to each other.

14. A method of performing a CT scan using the imaging system of claim 1, including:
- determining shape, size, and density information for the VOI in the examination region;
- positioning the wedge-shaped attenuation filter at a position in front of the X-ray source in accordance with gain of the detector and the shape, size and density information; and
- initiating CT data acquisition and gantry rotation.

15. The method according to claim 14, further including adjusting the position of the wedge-shaped attenuation filter relative to the X-ray source to maintain relatively uniform attenuation of X-rays as the gantry rotates around the VOI.

16. A method of generating a 3D image of a subject, including:
- evaluating a VOI in an examination region of an X-ray imaging device to determine size, shape, and density information about a portion of the VOI in the examination region;
- positioning an adjustable wedge-shaped attenuation filter at a position in a cone-shaped X-ray beam, the wedge-shaped attenuation filter being movable in front of the X-ray source, such that a first lateral portion of the filter has a first thickness exposed to the X-ray beam, and a second lateral portion of the filter has a second thickness exposed to the X-ray beam, wherein the first thickness is greater than the second thickness, and such that a middle portion of the filter extends from the first lateral portion to the second lateral portion and has a thickness exposed to the X-ray beam which continually decreases from the first thickness to the second thickness, and an entire lateral extent of the X-ray beam is disposed between the first lateral portion and the second lateral portion; and
- initiating CT data acquisition and gantry rotation.

17. The method according to claim 16, further including adjusting the position of the wedge-shaped attenuation filter relative to the X-ray source to maintain relatively uniform line integrals for X-ray paths through the VOI as the gantry rotates around the VOI.

18. The method according to claim 17, further including adjusting the position of the wedge-shaped attenuation filter closer to or further from the X-ray source.

19. The method according to claim 16, further including:
- converting X-rays that have traversed the VOI into imaging data; and
- reconstructing a 3D image of the VOI from the imaging data.

20. The method according to claim 16, wherein the X-ray source is mounted for rotation with the gantry and emits an X-ray cone beam across the examination region to an X-ray detector, generating a half field of view across the VOI and generating a complementary half field of view when the gantry is rotated 180°.

21. The method according to claim 16, further comprising adjusting the wedge-shaped attenuation filter as a function of VOI size, shape, and density information.

22. An apparatus for generating a 3D patient image, including:
- means for generating a cone-shaped X-ray beam which traverses half of a VOI, such that the beam traverses the other half of the VOI when rotated 180°;
- means for detecting the X-ray beam;
- means for adjustably attenuating of the X-ray beam including a filter comprising a first lateral portion having a first thickness exposed to the X-ray beam, a second lateral portion having a second thickness exposed to the X-ray beam wherein the first thickness is greater than the second thickness, and a middle portion extending from the first lateral portion to the second lateral portion and having a thickness exposed to the X-ray beam which continually decreases from the first thickness to the second thickness;
- means for monitoring size, shape, and density of the VOI presented to the X-ray beam during a 360° revolution of the X-ray generating means and means around the VOI; and
- means for selectively adjusting X-ray attenuation across an entire lateral extent of the X-ray beam between the first lateral portion and the second lateral portion of the filter by the attenuation means as the X-ray generation means and the detecting means rotate around the VOI.

* * * * *